United States Patent
Tanaka et al.

(10) Patent No.: US 11,400,053 B2
(45) Date of Patent: Aug. 2, 2022

(54) PATCH CONTAINING NONYLIC ACID VANILLYLAMIDE

(71) Applicant: HISAMITSU PHARMACEUTICAL CO., INC., Tosu (JP)

(72) Inventors: Yusuke Tanaka, Tosu (JP); Masahiro Sato, Tosu (JP); Takaaki Yoshinaga, Tosu (JP)

(73) Assignee: HISAMITSU PHARMACEUTICAL CO., INC., Tosu (JP)

(*) Notice: Subject to any disclaimer, the term of this patent is extended or adjusted under 35 U.S.C. 154(b) by 38 days.

(21) Appl. No.: 16/963,543

(22) PCT Filed: Jan. 23, 2019

(86) PCT No.: PCT/JP2019/001979
§ 371 (c)(1),
(2) Date: Jul. 21, 2020

(87) PCT Pub. No.: WO2019/146613
PCT Pub. Date: Aug. 1, 2019

(65) Prior Publication Data
US 2020/0352873 A1    Nov. 12, 2020

(30) Foreign Application Priority Data

Jan. 24, 2018 (JP) .............................. JP2018-009834

(51) Int. Cl.
| | |
|---|---|
| *A61K 9/70* | (2006.01) |
| *A61K 31/618* | (2006.01) |
| *A61K 47/02* | (2006.01) |
| *A61K 47/18* | (2017.01) |
| *A61K 31/05* | (2006.01) |
| *A61K 31/125* | (2006.01) |
| *A61K 36/534* | (2006.01) |

(52) U.S. Cl.
CPC ............ *A61K 9/7053* (2013.01); *A61K 31/05* (2013.01); *A61K 31/125* (2013.01); *A61K 31/618* (2013.01); *A61K 36/534* (2013.01); *A61K 47/02* (2013.01); *A61K 47/18* (2013.01)

(58) Field of Classification Search
CPC ....... A61F 7/03; A61K 31/045; A61K 31/125; A61K 33/08; A61K 47/02
See application file for complete search history.

(56) References Cited

U.S. PATENT DOCUMENTS

| | | | |
|---|---|---|---|
| 4,734,434 A | 3/1988 | Procaccini et al. | |
| 2006/0093656 A1 | 5/2006 | Muta et al. | |
| 2009/0238860 A1* | 9/2009 | Saeki ...................... | A61P 29/00 424/448 |
| 2011/0027326 A1 | 2/2011 | Hirayama | |
| 2011/0189307 A1 | 8/2011 | Bartels | |
| 2013/0243888 A1 | 9/2013 | Ford | |

FOREIGN PATENT DOCUMENTS

| | | | | |
|---|---|---|---|---|
| EP | 1632226 A1 * | 3/2006 | ............. | A61P 29/00 |
| JP | 59-110614 A | 6/1984 | | |
| JP | 10-298065 A | 11/1998 | | |
| JP | 2002-029993 A | 1/2002 | | |
| JP | 2007-045738 A | 2/2007 | | |
| JP | 2011-121866 A | 6/2011 | | |
| JP | 2015-098469 A | 5/2015 | | |
| WO | 2004/047820 A1 | 6/2004 | | |
| WO | 2017/146096 A1 | 8/2017 | | |

OTHER PUBLICATIONS

Kaken Pharmaceutical Co., Ltd., "Fulruban PAP 40mg", 6th edition, 2014, pp. 1-2.
International Search Report for PCT/JP2019/001979 dated Mar. 26, 2019 [PCT/ISA/210].
International Preliminary Report on Patentability dated Jul. 28, 2020 with Written Opinion from the International Bureau in International Application No. PCT/JP2019/001979.

* cited by examiner

*Primary Examiner* — Andrew S Rosenthal
*Assistant Examiner* — Lyndsey M Beckhardt
(74) *Attorney, Agent, or Firm* — Sughrue Mion, PLLC

(57) ABSTRACT

The present invention provides a patch comprising a backing layer and an adhesive agent layer, wherein the adhesive agent layer is non-aqueous, the adhesive agent layer contains nonylic acid vanillylamide and aluminum hydroxide, a content of nonylic acid vanillylamide in the adhesive agent layer is 0.01 to 0.025% by mass based on a total mass of the adhesive agent layer, a content of aluminum hydroxide in the adhesive agent layer is 0.55 to 1.5% by mass based on the total mass of the adhesive agent layer, and a mass ratio of the content of nonylic acid vanillylamide to the content of aluminum hydroxide ((content of nonylic acid vanillylamide):(content of aluminum hydroxide)) in the adhesive agent layer is 1:27 to 1:150.

4 Claims, No Drawings

PATCH CONTAINING NONYLIC ACID VANILLYLAMIDE

CROSS REFERENCE TO RELATED APPLICATIONS

This application is a National Stage of International Application No. PCT/JP2019/001979 filed Jan. 23, 2019, claiming priority based on Japanese Patent Application No. 2018-009834 filed Jan. 24, 2018.

TECHNICAL FIELD

The present invention relates to a patch, and more particularly to a patch containing nonylic acid vanillylamide.

BACKGROUND ART

As a preparation for the purpose of alleviating the symptoms of chronic diseases such as low back pain and stiff neck and upper back, warming sensation type external preparations for topically giving a warming sensation stimulus have been developed. It is considered that the warming sensation type external preparations exert an anti-inflammatory/analgesic effect on the chronic diseases by topically generating a thermal sensation using warming sensation stimulus ingredients, expanding the capillaries to promote blood circulation, and enhancing tissue metabolism.

Known examples of the warming sensation stimulus ingredients include capsicum extract, nonylic acid vanillylamide of synthetic capsicum, nicotinic acid ester, and the like. For example, Japanese Unexamined Patent Application Publication No. Hei 10-298065 (PTL 1) describes a patch in which a hydrophilic base layer containing water at 30 to 80% by weight is blended with at least one blood flow enhancer selected from vitamin E acetate, sodium polyethylene sulfonate, nonylic acid vanillylamide, capsicum extract, capsicum powder, capsicum tincture, capsaicin, benzyl nicotinate, and pelargonic acid.

However, for the purpose of continuously giving a warming sensation stimulus to the application site, the patch needs to contain a large amount of warming sensation stimulus ingredient. In addition, this also poses problems including the occurrence of skin irritation such as reddening due to a rash, and skin irritation remaining at the application site after the patch is removed. For example, as a patch for the purpose of solving such problems, International Publication No. WO2004/047820 (PTL 2) discloses a warming sensation poultice containing a warming sensation imparting substance, l-menthol, and polyethylene glycol.

In addition, for example, as a patch for the purpose of reducing skin irritation such as a rash, Japanese Unexamined Patent Application Publication No. 2007-45738 (PTL 3) discloses a patch which includes an adhesive base containing low molecular weight polyisobutylene at 3 to 30% by mass as well as aluminum hydroxide and/or titanium oxide.

CITATION LIST

Patent Literature

[PTL 1] Japanese Unexamined Patent Application Publication No. Hei 10-298065
[PTL 2] International Publication No. WO2004/047820
[PTL 3] Japanese Unexamined Patent Application Publication No. 2007-45738

SUMMARY OF INVENTION

Technical Problem

However, as a result of further studies on a patch or particularly a non-aqueous patch containing nonylic acid vanillylamide as a warming sensation stimulus ingredient, the present inventors have found that, depending on a skin symptom and the like of a patient, "itchiness" derived from a warming sensation stimulus ingredient, which is different from skin irritation such as a rash, may occur in rare cases at the application site. In addition, the present inventors have also found that even an ingredient conventionally known as an ingredient for suppressing skin irritation such as a rash is not always effective in suppressing such itchiness, and further that some of such ingredients and the like may have difficulty continuously giving an appropriate warming sensation stimulus to the application site.

The present invention has been made in view of the above problems, and an object thereof is to provide a non-aqueous patch which can give an appropriate warming sensation stimulus to the application site and can sufficiently suppress the occurrence of itchiness derived from the warming sensation stimulus ingredient.

Solution to Problem

The present inventors have made earnest studies to achieve the above object, and have found as a result that a patch comprising a backing layer and an adhesive agent layer is capable of giving an appropriate warming sensation stimulus to the application site and sufficiently suppressing the occurrence of itchiness derived from nonylic acid vanillylamide as the warming sensation stimulus ingredient, when the adhesive agent layer is substantially water-free, non-aqueous, and the adhesive agent layer contains a combination of nonylic acid vanillylamide and aluminum hydroxide in specific contents at a specific ratio. Thus, the present invention has been completed.

A patch of the present invention is a patch comprising a backing layer and an adhesive agent layer, wherein
  the adhesive agent layer is non-aqueous,
  the adhesive agent layer contains nonylic acid vanillylamide and aluminum hydroxide,
  a content of nonylic acid vanillylamide in the adhesive agent layer is 0.01 to 0.025% by mass based on a total mass of the adhesive agent layer,
  a content of aluminum hydroxide in the adhesive agent layer is 0.55 to 1.5% by mass based on the total mass of the adhesive agent layer, and
  a mass ratio of the content of nonylic acid vanillylamide to the content of aluminum hydroxide ((content of nonylic acid vanillylamide):(content of aluminum hydroxide)) in the adhesive agent layer is 1:27 to 1:150.

In the patch of the present invention, preferably, the adhesive agent layer is substantially water-free. In addition, preferably, the adhesive agent layer contains at least one anti-inflammatory analgesic agent selected from the group consisting of methyl salicylate, glycol salicylate, l-menthol, dl-camphor, peppermint oil, and thymol. More preferably, a content of the anti-inflammatory analgesic agent in the adhesive agent layer is 1 to 10% by mass based on the total mass of the adhesive agent layer.

Moreover, in the patch of the present invention, preferably, the adhesive agent layer contains at least one rubber-based adhesive base selected from the group consisting of styrene-isoprene-styrene block copolymers, polyisobutylene, styrene-butadiene-styrene block copolymers, natural rubber, polybutene, styrene-butadiene rubber, and isoprene.

Advantageous Effects of Invention

The present invention makes it possible to provide a non-aqueous patch which can give an appropriate warming sensation stimulus to the application site and can sufficiently suppress the occurrence of itchiness derived from the warming sensation stimulus ingredient.

DESCRIPTION OF EMBODIMENTS

Hereinafter, the present invention is described in detail based on its preferred embodiments. A patch of the present invention is a patch comprising a backing layer and an adhesive agent layer, wherein
the adhesive agent layer contains nonylic acid vanillylamide and aluminum hydroxide,
a content of nonylic acid vanillylamide in the adhesive agent layer is 0.01 to 0.025% by mass based on a total mass of the adhesive agent layer,
a content of aluminum hydroxide in the adhesive agent layer is 0.55 to 1.5% by mass based on the total mass of the adhesive agent layer, and
a mass ratio of the content of nonylic acid vanillylamide to the content of aluminum hydroxide ((content of nonylic acid vanillylamide):(content of aluminum hydroxide)) in the adhesive agent layer is 1:27 to 1:150.

The patch of the present invention includes a backing layer and an adhesive agent layer. The backing layer is not particularly limited as long as it can back the adhesive agent layer to be described later, and any known backing layer for patches can be appropriately used. Materials for the backing layer according to the present invention are illustrated by synthetic resins which include polyolefins such as polyethylene and polypropylene; ethylene-vinyl acetate copolymers, vinyl acetate-vinyl chloride copolymers, polyvinyl chloride, and the like; polyamides such as nylon; polyesters such as polyethylene terephthalate (PET), polybutylene terephthalate, and polyethylene naphthalate; cellulose derivatives; and polyurethane, as well as metals which include aluminum. Among these, polyesters and polyethylene terephthalate are preferable from the viewpoints of drug non-adsorption property and drug impermeable property. Examples of the form of the backing layer include films; sheet-shaped articles such as sheets, sheet-shaped porous bodies, and sheet-shaped foamed bodies; fabrics such as woven fabrics, knitted fabrics, and non-woven fabrics; foils; and laminates thereof. In addition, the thickness of the backing layer is not particularly limited, but is preferably in a range of 5 to 1000 μm from the viewpoints of workability when applying the patch and ease of production.

The patch of the present invention may further include a release liner on the surface of the adhesive agent layer opposite to the backing layer. The release liner is illustrated by a film, a sheet, and a laminate thereof, which are made of materials such as synthetic resins which include polyolefins such as polyethylene and polypropylene; ethylene-vinyl acetate copolymers, vinyl acetate-vinyl chloride copolymers, polyvinyl chloride, and the like; polyamides such as nylon; polyesters such as polyethylene terephthalate; cellulose derivatives; and polyurethane, as well as other materials such as aluminum and paper. Preferably, these release liners are subjected to a release treatment such as a silicone-containing compound coat or a fluorine-containing compound coat on the surface in contact with the adhesive agent layer so that they can be easily released from the adhesive agent layer.

The patch of the present invention is a non-aqueous patch, and the adhesive agent layer according to the present invention needs to be a non-aqueous adhesive agent layer. In the present invention, the "non-aqueous adhesive agent layer" means that the adhesive agent layer is substantially water-free, and examples of the water include purified water, sterilized water, natural water, and a mixture thereof. In the present invention, the phrase "substantially water-free" means that there is no step of intentionally blending water into the adhesive agent layer during the production step, and does not exclude moisture in the air or the like contained during the production step or moisture having absorbed sweat or the like during application of the patch to the skin. More specifically, the content of water in such an adhesive agent layer is preferably less than 1% by mass, more preferably 0.99% by mass or less, and further preferably 0 to 0.5% by mass based on the total mass of the adhesive agent layer.

The adhesive agent layer according to the present invention contains nonylic acid vanillylamide (also referred to as "nonylic acid vanillamide") as a warming sensation stimulus ingredient. In the present invention, the content of nonylic acid vanillylamide contained in the adhesive agent layer needs to be 0.01 to 0.025% by mass based on the total mass of the adhesive agent layer. In addition, the content of the nonylic acid vanillamide is more preferably 0.012 to 0.025% by mass, and further preferably 0.012 to 0.02% by mass. When the content of nonylic acid vanillylamide is less than the lower limit, the warming sensation stimulus given to the application site is insufficient and the thermal sensation tends to be lowered. Meanwhile, when the content of nonylic acid vanillylamide is more than the upper limit, the warming sensation stimulus given to the application site tends to be too strong, it becomes difficult to sufficiently suppress the occurrence of itchiness, and an unpleasant odor tends to occur.

The adhesive agent layer according to the present invention contains aluminum hydroxide. In the present invention, the content of aluminum hydroxide contained in the adhesive agent layer needs to be 0.55 to 1.5% by mass based on the total mass of the adhesive agent layer. In addition, the content of the aluminum hydroxide is more preferably 0.6 to 1.5% by mass, and further preferably 0.6 to 1.47% by mass. When the content of aluminum hydroxide is less than the lower limit, it tends to be difficult to sufficiently suppress the occurrence of itchiness. Meanwhile, when the content of aluminum hydroxide is more than the upper limit, the warming sensation stimulus given to the application site is insufficient and the thermal sensation tends to be lowered.

Moreover, in the present invention, the mass ratio of the content of nonylic acid vanillylamide to the content of aluminum hydroxide ((content of nonylic acid vanillylamide):(content of aluminum hydroxide)) in the adhesive agent layer needs to be 1:27 to 1:150. In addition, the mass ratio is more preferably 1:30 to 1:150, and further preferably 1:30 to 1:122.5. When the content of aluminum hydroxide relative to the content of nonylic acid vanillylamide is less than the lower limit, it becomes difficult to sufficiently suppress the occurrence of itchiness, and the warming sensation stimulus given to the application site tends to be too strong. Meanwhile, when the content of aluminum hydroxide relative to the content of nonylic acid vanillylamide is more than the upper limit, the warming sensation stimulus given to the application site is insufficient and the thermal sensation tends to be lowered.

Preferably, the adhesive agent layer according to the present invention further contains at least one anti-inflammatory analgesic agent selected from the group consisting of methyl salicylate, glycol salicylate, l-menthol, dl-camphor, peppermint oil, and thymol. By using these anti-inflammatory analgesic agents in combination with nonylic acid vanillylamide, it is possible to further improve the warming sensation stimulus derived from nonylic acid vanillylamide. Among these, the anti-inflammatory analgesic agent is preferably at least one selected from the group consisting of methyl salicylate, glycol salicylate, and l-menthol, and more preferably a combination of glycol salicylate and l-menthol, from the viewpoints of an appropriate anti-inflammatory analgesic effect and a tendency to give an appropriate stimulating sensation to the application site.

In the present invention, when the adhesive agent layer contains the anti-inflammatory analgesic agent, the content of the anti-inflammatory analgesic agent contained in the adhesive agent layer (in the case of two or more kinds, the total content thereof, and the same applies hereinafter) is preferably 1 to 10% by mass, more preferably 1.5 to 9% by mass, and further preferably 2.55 to 7.66% by mass based on the total mass of the adhesive agent layer. When the content of the anti-inflammatory analgesic agent is less than the lower limit, the anti-inflammatory analgesic effect tends to be insufficient. Meanwhile, when the content of the anti-inflammatory analgesic agent is more than the upper limit, it tends to be difficult to uniformly contain it in the adhesive agent layer.

The adhesive base of the adhesive agent layer according to the present invention is not particularly limited as long as it is substantially water-free, and examples thereof include a rubber-based adhesive base, an acrylic adhesive base, and a silicone-based adhesive base.

Examples of the rubber-based adhesive base include styrene-isoprene-styrene block copolymers (SIS), polyisobutylene (PIB), isoprene, styrene-butadiene-styrene block copolymers (SBS), styrene-butadiene rubber (SBR), polybutene, and natural rubber, and one of these may be used alone, or two or more thereof may be used in combination. Among these, from the viewpoints of good adhesiveness to the skin and the tendency to be able to give an appropriate warming sensation stimulus to the application site, the rubber-based adhesive base used is preferably at least one selected from the group consisting of styrene-isoprene-styrene block copolymers and polyisobutylene, and is more preferably a styrene-isoprene-styrene block copolymer or a combination of styrene-isoprene-styrene block copolymer and polyisobutylene. When a styrene-isoprene-styrene block copolymer and polyisobutylene are used in combination, the mass ratio of the styrene-isoprene-styrene block copolymer to the polyisobutylene ((mass of SIS):(mass of PIB)) is more preferably 1:0.281 to 1:0.587 (further preferably in the range of 1:0.338 to 1:0.431), for example.

Examples of the acrylic adhesive base include acrylic acid/acrylic acid octyl ester copolymer, 2-ethylhexyl acrylate/vinylpyrrolidone copolymer, acrylic ester/vinyl acetate copolymer, 2-ethylhexyl acrylate/2-ethylhexylmethacrylate/dodecyl methacrylate copolymer, methyl acrylate/2-ethylhexyl acrylate copolymer resin, 2-ethylhexyl acrylate/methyl acrylate/acrylic acid/glycidyl methacrylate copolymer, 2-ethylhexyl acrylate/vinyl acetate/hydroxyethyl acrylate/glycidyl methacrylate copolymer, 2-ethylhexyl acrylate/diacetone acrylamide/acetoacetoxyethyl methacrylate/methyl methacrylate copolymer, ethyl acrylate/methyl methacrylate copolymer, and acrylic polymer contained in an acrylic resin alkanolamine liquid, which are listed in "Iyakuhin Tenkabutu Jiten 2016 (edited by Nippon Iyakuhin Tenka Zai Kyokai)" as adhesive agents, and one of these may be used alone, or two or more thereof may be used in combination.

Examples of the silicone-based adhesive base include polydimethyl siloxane (such as a polymer represented by MQ in ASTM D-1418), polymethyl vinyl siloxane (such as a polymer represented by VMQ in ASTM D-1418), and polymethyl phenyl siloxane (such as a polymer represented by PVMQ in ASTM D-1418), and one of these may be used alone, or two or more thereof may be used in combination.

Among these, the adhesive base of the adhesive agent layer according to the present invention is preferably the rubber-based adhesive base, and more preferably at least one rubber-based adhesive base selected from the group consisting of styrene-isoprene-styrene block copolymers and polyisobutylene.

In the present invention, the content of these adhesive bases (in the case of two or more kinds, the total content thereof, and the same applies hereinafter) is more preferably 10 to 50% by mass, and further preferably 20 to 40% by mass based on the total mass of the adhesive agent layer. When the content of the adhesive base is less than the lower limit, the cohesiveness of the adhesive agent layer tends to be lowered. Meanwhile, when the content of the adhesive base is more than the upper limit, the adhesiveness to the skin tends to be lowered.

Preferably, the adhesive agent layer according to the present invention further contains a tackifier particularly when it contains the rubber-based adhesive base as the adhesive base. The tackifier is blended mainly for the purpose of increasing the tackiness of the adhesive base.

Examples of the tackifier include rosin-based resin, terpene-based resin, petroleum-based resin (such as alicyclic saturated hydrocarbon resin which is a homopolymer or copolymer of an alicyclic hydrocarbon monomer), phenol-based resin, and xylene-based resin, and one of these may be used alone, or two or more thereof may be used in combination.

The rosin-based resin is a resin whose main ingredient is rosin acid. When the adhesive agent layer according to the present invention contains the rosin-based resin, examples of the rosin-based resin include hydrogenated rosin glycerin ester, ultralight rosin, ultralight rosin ester, and acid-modified ultralight rosin, and one of these may be used alone, or two or more thereof may be used in combination. As the rosin-based resin, commercially available products such as PINECRYSTAL (such as KE-311, PE-590, KE-359, and KE-100) (trade name, manufactured by Arakawa Chemical Industries, Ltd.) may be appropriately used, and one of these may be used alone, or two or more thereof may be used in combination.

The terpene-based resin is a resin having isoprene as a constituent unit. When the adhesive agent layer according to the present invention contains the terpene-based resin, examples of the terpene-based resin include pinene polymers (such as α-pinene polymer and β-pinene polymer), terpene polymers, dipentene polymers, terpene-phenol polymers, aromatic modified terpene polymers, and pinene-phenol copolymers, and one of these may be used alone, or two or more thereof may be used in combination. As the terpene-based resin, commercially available products such as YS RESIN (such as YS RESIN PXN, YS RESIN PX1150N, YS RESIN PX1000, YS RESIN TO125, and YS RESIN TO105), CLEARON P105, CLEARON M115, CLEARON K100 (these are trade names, manufactured by YASUHARA CHEMICAL CO., LTD.), and TAMANOL 901 (trade name, manufactured by Arakawa Chemical Industries, Ltd.) may be appropriately used, and one of these may be used alone, or two or more thereof may be used in combination.

Among these, from the viewpoints of good adhesiveness to the skin and the tendency to be able to give an appropriate warming sensation stimulus to the application site, the tackifier is preferably at least one selected from the group consisting of the rosin-based resins and the terpene-based resins, and more preferably at least one selected from the group consisting of hydrogenated rosin glycerin esters and pinene polymers.

In the present invention, when the adhesive agent layer contains the tackifier, the content of the tackifier contained in the adhesive agent layer (in the case of two or more kinds, the total content thereof, and the same applies hereinafter) is preferably 10 to 50% by mass, more preferably 10 to 30% by mass, and further preferably 15 to 30% by mass based on the total mass of the adhesive agent layer. When the content of the tackifier is less than the lower limit, sufficient adhesiveness to the skin is not exhibited. Meanwhile, when the content of the tackifier is more than the upper limit, sufficient cohesiveness of the adhesive agent layer may not be exhibited, or pain at the time of removing the patch tends to increase.

The adhesive agent layer according to the present invention may further contain an absorption enhancer (transdermal absorption enhancer) having an action of promoting transdermal absorption of active ingredients. Examples of the absorption enhancer include aliphatic alcohols, fatty acids having 6 to 20 carbon atoms, fatty acid esters, fatty acid amides, or aliphatic alcohol ethers; aromatic organic acids; aromatic alcohols; aromatic organic acid esters or ethers; POE hydrogenated castor oils; lecithins; phospholipids; soybean oil derivatives; and triacetin, and one of these may be used alone, or two or more thereof may be used in combination.

In the present invention, when the adhesive agent layer contains the absorption enhancer, the content of the absorption enhancer contained in the adhesive agent layer (in the case of two or more kinds, the total content thereof, and the same applies hereinafter) is preferably 15% by mass or less, more preferably 12% by mass or less, and further preferably 10% by mass or less based on the total mass of the adhesive agent layer.

In addition, the adhesive agent layer according to the present invention may further contain an additional active ingredient other than nonylic acid vanillylamide and the anti-inflammatory analgesic agent described above, an antioxidant, a plasticizer, a filler, a solubilizer, and the like in an appropriate amount if necessary, as long as the effects of the present invention are not impaired.

Examples of the additional active ingredient other than nonylic acid vanillylamide and the anti-inflammatory analgesic agent described above include plant-derived ingredients such as Amur cork tree powder and glycyrrhetinic acid; and medicinal ingredients such as non-steroidal anti-inflammatory analgesic agents (such as diclofenac, indomethacin, ketoprofen, felbinac, loxoprofen, ibuprofen, flurbiprofen, tiaprofen, acemetacin, sulindac, etodolac, tolmetin, piroxicam, meloxicam, ampiroxicam, naproxen, azapropazone, valdecoxib, celecoxib, rofecoxib, and amfenac), antipyretic analgesic drugs (such as acetaminophen), antihistaminic agents (such as diphenhydramine, chlorpheniramine, mequitazine, and homochlorcyclizine), antihypertensive agents (such as diltiazem, nicardipine, nilvadipine, metoprolol, bisoprolol, and trandolapril), Anti-Parkinsonian agents (such as pergolide, ropinirole, bromocriptine, and selegiline), bronchodilating agents (such as tulobuterol, isoproterenol, and salbutamol), antiallergic agents (such as ketotifen, loratadine, azelastine, terfenadine, cetirizine, and acitazanolast), topical anesthetic agents (such as lidocaine and dibucaine), neuropathic pain treatment drugs (such as pregabalin), non-narcotic analgesic drugs (buprenorphine, tramadol, and pentazocine), anesthesia-based analgesic agents (such as morphine, oxycodone, and fentanyl), urinary organ affecting agents (such as oxybutynin and tamsulosin), brain-nerve affecting agents (such as promazine and chlorpromazine), steroid hormone agents (such as estradiol, progesterone, norethisterone, cortisone, and hydrocortisone), antidepressant agents (such as sertraline, fluoxetine, paroxetine, and citalopram), anti-dementia drugs (such as donepezil, rivastigmine, and galantamine), antipsychotic drugs (such as risperidone and olanzapine), central nervous system stimulating agents (such as methylphenidate), osteoporosis treatment drugs (such as raloxifene and alendronate), breast cancer preventive drugs (such as tamoxifen), anti-obesity drugs (such as mazindol and sibutramine), insomnia-improving drugs (such as melatonin), and anti-rheumatic drugs (such as actarit), and one of these may be used alone, or two or more thereof may be used in combination.

In the present invention, when the adhesive agent layer contains the additional active ingredient, the content of the additional active ingredient contained in the adhesive agent layer (in the case of two or more kinds, the total content thereof, and the same applies hereinafter) is preferably 5% by mass or less, more preferably 0.5 to 5% by mass, further preferably 0.5 to 4% by mass, and still more preferably 1 to 3% by mass based on the total mass of the adhesive agent layer, although it cannot be said unconditionally because the content is adjusted appropriately depending on the purpose of treatment.

Examples of the antioxidant include ascorbic acid, propyl gallate, butylhydroxyanisole, dibutylhydroxytoluene, nordihydroguaiaretic acid, tocopherol, tocopherol acetate, and sodium hydrogen sulfite, and one of these may be used alone, or a mixture of two or more may be used.

In the present invention, when the adhesive agent layer contains the antioxidant, the content of the antioxidant contained in the adhesive agent layer (in the case of two or more kinds, the total content thereof, and the same applies hereinafter) is, for example, preferably 5% by mass or less, more preferably 0.1 to 5% by mass, further preferably 3% by mass or less, and still more preferably 0.1 to 1% by mass based on the total mass of the adhesive agent layer.

Examples of the plasticizer include silicone oils; petroleum-based oils such as paraffinic process oils, naphthenic process oils, and aromatic process oils; squalane and squalene; vegetable-based oils such as olive oil, camellia oil, castor oil, tall oil, and peanut oil; dibasic acid esters such as dibutyl phthalate and dioctyl phthalate; liquid rubbers such as polybutene and liquid isoprene rubber; and diethylene glycol, polyethylene glycol, propylene glycol, and dipropylene glycol, and one of these may be used alone, or two or more thereof may be used in combination. Among these, the plasticizer is preferably at least one selected from the group consisting of silicone oils, liquid paraffin, and liquid polybutene.

In the present invention, when the adhesive agent layer contains the plasticizer, the content of the plasticizer contained in the adhesive agent layer (in the case of two or more kinds, the total content thereof, and the same applies hereinafter) is, for example, preferably 15 to 50% by mass, more preferably 20 to 45% by mass, and further preferably 22 to 43% by mass based on the total mass of the adhesive agent layer.

Examples of the filler include carbonates such as calcium carbonate and magnesium carbonate; silicates such as magnesium silicate; silicic acid, aluminum silicate, barium sulfate, calcium sulfate, calcium zincate, zinc oxide, and titanium oxide, and one of these may be used alone, or two or more thereof may be used in combination. Among these, preferably, the filler is at least one selected from the group consisting of titanium oxide and aluminum silicate.

In the present invention, when the adhesive agent layer contains the filler, the content of the filler contained in the adhesive agent layer (in the case of two or more kinds, the total content thereof, and the same applies hereinafter) is, for example, preferably 5% by mass or less, more preferably 0.5 to 5% by mass, further preferably 0.5 to 3.5% by mass, and still more preferably 1 to 3% by mass based on the total mass of the adhesive agent layer.

Examples of the solubilizer include benzyl alcohol; pirotiodecane; isopropyl myristate; crotamiton; pyrrolidones such as N-methyl-2-pyrrolidone; higher alcohols; and polybasic acids such as diethyl adipate, isopropyl adipate, diisopropyl adipate, diisobutyl adipate, dioctyl adipate, di(2-heptylundecyl)adipate, diisopropyl sebacate, and diethyl sebacate, and one of these may be used alone, or two or more thereof may be used in combination.

In the present invention, when the adhesive agent layer contains the solubilizer, the content of the solubilizer contained in the adhesive agent layer (in the case of two or more kinds, the total content thereof, and the same applies hereinafter) is, for example, preferably 10% by mass or less based on the total mass of the adhesive agent layer.

The adhesive agent layer according to the present invention is not particularly limited, but the total mass per unit area (area of the application surface) is preferably 80 to 400 g/m$^2$, and more preferably 110 to 380 g/m$^2$. In addition, the area of the application surface of the adhesive agent layer according to the present invention can be appropriately adjusted according to the purpose of treatment and the target of application, and is not particularly limited, but is usually in the range of 0.5 to 200 cm$^2$. Moreover, the shape of the application surface of the adhesive agent layer according to the present invention is not particularly limited, and it is possible to employ any shape such as a round shape, an elliptical shape, a square shape, and a rectangular shape.

The patch of the present invention is not particularly limited, and can be produced by appropriately employing a known method for producing a non-aqueous patch. For example, first, nonylic acid vanillylamide, aluminum hydroxide, the above-described adhesive base, and, if necessary, the above-described additional ingredients are mixed in a usual manner to obtain a uniform adhesive agent layer composition. Next, this adhesive agent layer composition is applied on the surface (usually on one surface) of the backing layer to the desired mass per unit area, which is then cut into a desired shape if necessary. Thereby, the patch of the present invention can be obtained.

In addition, the method for producing the patch of the present invention may further include a step of attaching the release liner on the surface of the adhesive agent layer opposite to the backing layer. Further, the method for producing the patch of the present invention may include steps of first applying the adhesive agent layer composition on one surface of the release liner to the desired mass per unit area to form an adhesive agent layer, then attaching the backing layer on the surface of the adhesive agent layer opposite to the release liner, and cutting it into a desired shape if necessary, to thereby obtain the patch of the present invention. Moreover, the obtained patch may be, if necessary, enclosed in a packaging container for storage (for example, an aluminum laminated bag) to form a package.

EXAMPLES

Hereinafter, the present invention is described more specifically based on Examples and Comparative Examples, but the present invention is not limited to the following Examples. Note that, in each of the Examples and Comparative Examples, the itchiness evaluation and warming sensation stimulus evaluation tests were performed by the methods described below.

<Itchiness Evaluation and Warming Sensation Stimulus Evaluation Tests>

Each of the patches was cut into circles having a diameter of 40 mm to release the release liners. One patch was applied to the shoulder skin of each of 6 to 30 subjects for 120 minutes. The subjects evaluated the itchiness of the application site during application according to the following itchiness evaluation criteria:

[Itchiness Evaluation]
0: No itchiness is felt
5: Very slight itchiness is felt
10: Slight itchiness is felt
20: Itchiness is somewhat felt
25: Itchiness is felt but acceptable
30: Somewhat unacceptable itchiness is felt
35: Unacceptable itchiness is felt
40: Itchiness with pain is felt.

In addition, the subjects evaluated the warming sensation stimulus of the application site during the application according to the following criteria for warming sensation stimulus evaluation.

[Warming Sensation Stimulus Evaluation]
0: No warming sensation stimulus is felt
25: A warming sensation stimulus is felt, but is weak
40: A warming sensation stimulus is felt, but is somewhat weak
50: A moderate warming sensation stimulus is felt
60: A warming sensation stimulus is somewhat strongly felt
75: A warming sensation stimulus is strongly felt
100: Too strong a warming sensation stimulus is felt.

Regarding the evaluation values for each of the itchiness evaluation and the warming sensation stimulus evaluation obtained from the subjects, the sum of the obtained values was divided by the number of the subjects to calculate the average value, which was used as a value for the evaluation. Note that, in the itchiness evaluation, a value of less than 25 is recognized as having no problem as the itchiness, and in the warming sensation stimulus evaluation, a value of 40 or more and less than is recognized as having an appropriate warming sensation stimulus as the warming sensation stimulus.

Example 1

First, 0.012 parts by mass of nonylic acid vanillylamide, 1.70 parts by mass of Amur cork tree powder, 2.55 parts by mass of glycol salicylate, 5.11 parts by mass of l-menthol, 27.24 parts by mass of styrene-isoprene-styrene block copolymer, 10.00 parts by mass of polyisobutylene, 22.0 parts by mass of terpene-based resin, 27.49 parts by mass of liquid paraffin, 0.43 parts by mass of antioxidant (tocopherol acetate), 1.47 parts by mass of aluminum hydroxide, and 2.00 parts by mass of additional ingredient (filler) were mixed to obtain an adhesive agent layer composition. Then, the obtained adhesive agent layer composition was applied onto a release liner (a polyethylene terephthalate film subjected to a release treatment) to form an adhesive agent layer having a mass per unit area of 294 g/m$^2$. A backing layer (polyethylene terephthalate film) was laminated on the surface of the obtained adhesive agent layer opposite to the release liner to obtain a patch in which backing layer/adhesive agent layer/release liner were laminated in this order.

Examples 2 to 4 and Comparative Examples 1 and 2

Each of the patches was obtained in the same manner as in Example 1 except that the compositions of the adhesive agent layer compositions were changed to the compositions presented in Table 1 below. In Tables 1 and 2 below, PINECRYSTAL (manufactured by Arakawa Chemical Industries, Ltd.) was used as the rosin-based resin.

The patches obtained in Examples 1 to 4 and Comparative Examples 1 and 2 were subjected to itchiness evaluation and warming sensation stimulus evaluation tests. The results are presented in Table 1 below together with the compositions of the adhesive agent layer compositions of Examples and Comparative Examples.

As clear from the results presented in Table 1, it was confirmed that the patch of the present invention could sufficiently suppress the occurrence of itchiness at the application site and could maintain the warming sensation stimulus within an appropriate range. On the other hand, when the content of aluminum hydroxide based on nonylic acid vanillylamide was small (Comparative Example 1), and when aluminum silicate conventionally known as a skin irritation suppressing ingredient for a rash and the like was used instead of aluminum hydroxide (Comparative Example 2), it was confirmed that the evaluation value of itchiness evaluation was significantly higher than that of the patch of the present invention. In addition, it was confirmed that, even when the aluminum hydroxide was contained, the evaluation value of warming sensation stimulus evaluation was out of the appropriate range either, if the content thereof was out of the range according to the present invention (Comparative Example 1).

Examples 5 to 9 and Comparative Examples 3 to 6

Each of the patches was obtained in the same manner as in Example 1 except that the compositions of the adhesive agent layer compositions were changed to the compositions presented in Table 2 below.

The patches obtained in Examples 5 to 9 and Comparative Examples 3 to 6 were subjected to itchiness evaluation and warming sensation stimulus evaluation tests. The results are presented in Table 2 below together with the compositions of the adhesive agent layer compositions of Examples and Comparative Examples.

TABLE 1

|  | Ex. 1 | Ex. 2 | Ex. 3 | Ex. 4 | Comp. Ex. 1 | Comp. Ex. 2 |
| --- | --- | --- | --- | --- | --- | --- |
| Adhesive Agent Layer Composition [Parts by Mass] | | | | | | |
| Nonylic Acid Vanillylamide | 0.012 | 0.012 | 0.02 | 0.02 | 0.02 | 0.02 |
| Amur Cork Tree Powder | 1.70 | 1.70 | 1.70 | 1.70 | 1.70 | 1.70 |
| Glycol Salicylate | 2.55 | 2.55 | 2.55 | 2.55 | 2.55 | 2.55 |
| 1-Menthol | 5.11 | 5.11 | 5.11 | 5.11 | 5.11 | 5.11 |
| Styrene-Isoprene-Styrene Block Copolymer | 27.24 | 21.79 | 27.24 | 23.54 | 23.84 | 25.00 |
| Polyisobutylene | 10.00 | 9.40 | 10.00 | 8.22 | 8.02 | 11.50 |
| Terpene-Based Resin | 22.00 | 8.00 | 22.00 | 8.00 | 8.00 | 22.00 |
| Rosin-Based Resin | — | 14.00 | — | 14.00 | 14.00 | — |
| Liquid Paraffin | 27.49 | 33.83 | 27.48 | 33.83 | 33.83 | 26.82 |
| Antioxidant | 0.43 | 0.43 | 0.43 | 0.43 | 0.43 | 2.03 |
| Aluminum Hydroxide | 1.47 | 1.18 | 1.47 | 0.60 | 0.50 | — |
| Aluminum Silicate | — | — | — | — | — | 1.27 |
| Additional Ingredient | 2.00 | 2.00 | 2.00 | 2.00 | 2.00 | 2.00 |
| Total | 100 | 100 | 100 | 100 | 100 | 100 |
| (Nonylic Acid Vanillylamide):(Aluminum Hydroxide) [Mass Ratio] | 1:122.5 | 1:98.3 | 1:73.5 | 1:30 | 1:25 | — |
| Evaluation | | | | | | |
| Itchiness | 18.7 | 17.2 | 13.6 | 16.5 | 26.4 | 35.9 |
| Warming Sensation Stimulus | 58.7 | 51.5 | 57.2 | 57.5 | 62.9 | 51.3 |

TABLE 2

|  | Comp. Ex. 3 | Ex. 5 | Comp. Ex. 4 | Ex. 6 | Ex. 7 | Comp. Ex. 5 | Ex. 8 | Ex. 9 | Comp. Ex. 6 |
|---|---|---|---|---|---|---|---|---|---|
| Adhesive Agent Layer Composition [Parts by Mass] | | | | | | | | | |
| Nonylic Acid Vanillylamide | 0.016 | 0.016 | 0.030 | 0.025 | 0.025 | 0.025 | 0.010 | 0.010 | 0.010 |
| Amur Cork Tree Powder | 1.70 | — | 1.70 | 1.70 | 1.70 | 1.70 | 1.70 | 1.70 | 1.70 |
| Glycol Salicylate | 2.55 | — | 2.55 | 2.55 | 2.55 | 2.55 | 2.55 | 2.55 | 2.55 |
| 1-Menthol | 5.11 | — | 5.11 | 5.11 | 5.11 | 5.11 | 5.11 | 5.11 | 5.11 |
| Styrene-Isoprene-Styrene Block Copolymer | 21.79 | 24.24 | 21.79 | 21.79 | 21.79 | 21.79 | 21.79 | 21.79 | 21.79 |
| Polyisobutylene | 9.40 | 10.46 | 9.40 | 9.40 | 9.40 | 9.40 | 9.40 | 9.40 | 9.40 |
| Terpene-Based Resin | 8.00 | 8.90 | 8.00 | 8.00 | 8.00 | 8.00 | 8.00 | 8.00 | 8.00 |
| Rosin-Based Resin | 14.00 | 15.58 | 14.00 | 14.00 | 14.00 | 14.00 | 14.00 | 14.00 | 14.00 |
| Liquid Paraffin | 33.82 | 37.62 | 33.49 | 33.50 | 34.32 | 34.45 | 33.51 | 34.46 | 35.01 |
| Antioxidant | 0.43 | — | 0.43 | 0.43 | 0.43 | 0.43 | 0.43 | 0.43 | 0.43 |
| Aluminum Hydroxide | — | 1.18 | 1.50 | 1.50 | 0.68 | 0.55 | 1.50 | 0.55 | — |
| Aluminum Silicate | 1.18 | — | — | — | — | — | — | — | — |
| Additional Ingredient | 2.00 | 2.00 | 2.00 | 2.00 | 2.00 | 2.00 | 2.00 | 2.00 | 2.00 |
| Total | 100 | 100 | 100 | 100 | 100 | 100 | 100 | 100 | 100 |
| (Nonylic Acid Vanillylamide):(Aluminum Hydroxide) [Mass Ratio] | — | 1:73.8 | 1:50 | 1:60 | 1:27.2 | 1:22 | 1:150 | 1:55 | — |
| Evaluation | | | | | | | | | |
| Itchiness | 31.5 | 8.6 | 25.3 | 15.7 | 15.8 | 28.8 | 14.3 | 17.1 | 25.9 |
| Warming Sensation Stimulus | 45.0 | 58.3 | 67.5 | 57.9 | 59.2 | 59.2 | 52.0 | 51.0 | 44.3 |

As also clear from the results presented in Table 2, it was confirmed that the patch of the present invention could sufficiently suppress the occurrence of itchiness at the application site and could maintain the warming sensation stimulus within an appropriate range. On the other hand, also when aluminum hydroxide was not contained (Comparative Example 6) and magnesium hydroxide was used instead of aluminum hydroxide, as a same hydroxide of a metal (Comparative Example 3), it was confirmed that the evaluation value of itchiness evaluation was higher than that of the patch of the present invention, failing to suppress the occurrence of itchiness.

Further, as clear from the comparison between Examples 6 and 7 and Comparative Example 4, and the comparison among Examples 6 and 7, Comparative Example 5, and Examples 8 and 9, the following was confirmed. In the patch of the present invention, wherein the content of aluminum hydroxide was within a specific range (0.55 to 1.5% by mass based on the total mass of the adhesive agent layer), the content of nonylic acid vanillylamide was within a specific range (0.01 to 0.025% by mass based on the total mass of the adhesive agent layer), and the mass ratio of the content of nonylic acid vanillylamide to the content of aluminum hydroxide was also within a specific range ((content of nonylic acid vanillylamide):(content of aluminum hydroxide)=1:27 to 1:150), this made it possible to sufficiently suppress the occurrence of itchiness and to maintain the warming sensation stimulus within an appropriate range. On the other hand, if anyone of these conditions was not satisfied (for example, Comparative Example 4 and Comparative Example 5), the evaluation value of itchiness evaluation was high, failing to suppress the occurrence of itchiness.

INDUSTRIAL APPLICABILITY

As described above, the present invention makes it possible to provide a non-aqueous patch which can give an appropriate warming sensation stimulus to the application site and can sufficiently suppress the occurrence of itchiness derived from the warming sensation stimulus ingredient.

The invention claimed is:

1. A patch comprising a backing layer and an adhesive agent layer, wherein
   the adhesive agent layer is non-aqueous,
   the adhesive agent layer contains nonylic acid vanillylamide, aluminum hydroxide and a tackifier wherein the tackifier is at least one selected from the group consisting of a rosin-based resin and a terpene-based resin,
   a content of nonylic acid vanillylamide in the adhesive agent layer is 0.012 to 0.025% by mass based on a total mass of the adhesive agent layer,
   a content of aluminum hydroxide in the adhesive agent layer is 0.55 to 1.5% by mass based on the total mass of the adhesive agent layer, and
   a mass ratio of the content of nonylic acid vanillylamide to the content of aluminum hydroxide ((content of nonylic acid vanillylamide):(content of aluminum hydroxide)) in the adhesive agent layer is 1:27 to 1:150.

2. The patch according to claim 1, wherein the adhesive agent layer contains at least one anti-inflammatory analgesic agent selected from the group consisting of methyl salicylate, glycol salicylate, l-menthol, dl-camphor, peppermint oil, and thymol.

3. The patch according to claim 2, wherein a content of the anti-inflammatory analgesic agent in the adhesive agent layer is 1 to 10% by mass based on the total mass of the adhesive agent layer.

4. The patch according to claim 1, wherein the adhesive agent layer contains at least one rubber-based adhesive base selected from the group consisting of styrene-isoprene-styrene block copolymers, polyisobutylene, styrene-butadiene-styrene block copolymers, natural rubber, polybutene, styrene-butadiene rubber, and isoprene.

* * * * *